US006702770B2

(12) United States Patent
Bremer et al.

(10) Patent No.: US 6,702,770 B2
(45) Date of Patent: Mar. 9, 2004

(54) POSTERIOR LUMBAR LORDOSIS ORTHOTIC DEVICE

(75) Inventors: Ross L. Bremer, Atlantic Beach, FL (US); Richard Coleman, Ponte Vedra, FL (US); Nolan Hill, Jacksonville, FL (US); Kurt Wullenweber, Yulee, FL (US)

(73) Assignee: The Bremer Group Company, Jacksonville, FL (US)

( * ) Notice: Subject to any disclaimer, the term of this patent is extended or adjusted under 35 U.S.C. 154(b) by 100 days.

(21) Appl. No.: 10/101,597

(22) Filed: Mar. 21, 2002

(65) Prior Publication Data

US 2003/0181839 A1 Sep. 25, 2003

(51) Int. Cl.[7] ................................................. A61F 5/00
(52) U.S. Cl. ............................................ 602/5; 602/19
(58) Field of Search ............................ 602/5, 19; 2/44, 2/45; 128/96.1, 99.1, 106.1, 107.1, 112.1

(56) References Cited

U.S. PATENT DOCUMENTS

| 2,453,370 A | * 11/1948 | Hittenberger ................ 602/19 |
| 3,351,053 A | * 11/1967 | Stuttle ......................... 602/19 |
| 3,548,817 A | * 12/1970 | Mittasch ...................... 602/19 |
| 5,718,670 A | 2/1998 | Bremer |
| 5,782,782 A | * 7/1998 | Miller ............................. 2/44 |
| 5,853,378 A | 12/1998 | Modglin |
| 6,190,343 B1 | 2/2001 | Heinz et al. |
| 6,213,968 B1 | 4/2001 | Heinz et al. |

OTHER PUBLICATIONS

U.S. Patent Publication No. 2001/0020144, Heinz et al., Sep. 6, 2001.
U.S. Patent Publication No. 2001/0008955, Garth, Jul. 19, 2001.

* cited by examiner

Primary Examiner—Michael A. Brown
(74) Attorney, Agent, or Firm—Nixon & Vanderhye (57) ABSTRACT

A posterior lumbar lordosis orthotic device includes front and back panels and sides. The back panel is shaped to simulate the lordosis of an individual and has upper and lower regions angularly related to one another. Screws accessible from the inside of the back panel are rotatable to adjust the angle between the upper and lower regions to more closely accommodate the specific lordosis of an individual. The front panel is secured to the sides, using modified pop rivets, enabling the front panel and sides to be adjustably secured to one another to adjust the overall girth of the device and to differentially adjust the girth along upper and lower portions of the device to accommodate individuals of different waist and hip sizes.

22 Claims, 8 Drawing Sheets

POSTERIOR LUMBAR LORDOSIS ORTHOTIC DEVICE

BACKGROUND OF THE INVENTION

The present invention relates to an orthotic device for treatment of spinal disorders and particularly relates to a posterior lumbar lordosis orthotic device for adjustably bracing the back of an individual.

Orthotic devices for supporting and bracing an individual's back are numerous, well known and effective for maintaining the stability of the spine and particularly the lumbar region. However, difficulties are encountered in fitting such orthotic devices to various individuals. For example, individuals have varying degrees of lordosis, as well as a wide variety of girths about their torsos. Also, orthotic devices are typically sized differently for male and female individuals. Even within one gender, however, there are varying degrees of lordosis and girths about the upper torso, waist and hip areas. A common problem has been to fit the orthotic device to the particular individual and the individual's spinal curvature, as well as to accommodate the different sizes of individuals, i.e., girths about the torso including waists and hips.

It is possible to customize an orthotic device to an individual's anatomy. This, however, involves significant expense. A variety of orthotic devices have been proposed and constructed for adjusting the girth about an individual's torso but have not afforded differential growth adjustment to accommodate individuals of different upper torso, waist and hip sizes, keeping in mind that each individual has a unique girth and a unique lordosis. Consequently, there has developed a need for an orthotic device which is adjustable to accommodate an individual's posterior lumbar lordosis, as well as differences in sizing between individuals of each gender and the unique anatomy of each individual.

BRIEF DESCRIPTION OF THE INVENTION

In accordance with a preferred embodiment of the present invention, there is provided an orthotic device which is adjustable to accommodate the unique lordosis and anatomy of individuals of both genders. To accomplish the foregoing, there is provided, in a preferred embodiment, an orthotic body having back and front panels and sides interconnecting the back and front panels for encompassing an individual's torso. The back panel has upper and lower regions angularly related to one another generally corresponding to the posterior lumbar lordosis of an average individual. The average lordosis for individuals is about 10–20°. Lordosis is measured in degrees as the combined deviations of the upper and lower back regions from a vertical plane through the waist. The back panel is provided with an adjustment mechanism to alter the angle between the upper and lower regions of the back panel to shape the back panel to the unique and desired shape of an individual's back (lordosis). The adjustment mechanism preferably includes a coupling extending between the upper and lower regions of the back panel and which coupling is adjustable to change the angle between the upper and lower regions, thereby adjusting the back panel uniquely to an individual's lordosis. Particularly, the adjustment mechanism includes at least one rod, and preferably two rods, extending between reinforcements on respective upper and lower regions of the back panel. The rod, e.g., a bolt, has screw threads cooperable with mating screw threads on the back panel, to adjust the angle of the upper and lower regions relative to the vertical, i.e., to adjust to the individual's lordosis.

Further, to accommodate various sizes and the different anatomies of individuals within each gender, the front panel is secured to at least one of the sides such that the gross girth of the orthotic body can be adjusted. Additionally, a pair of fastening elements vertically spaced from one another are provided between the front panel and at least one side such that the girth at different elevations along the orthotic device can be adjusted. For example, the girth at the waist of the individual can be reduced, while the girth along the hip region can be enlarged by a differential placement of the fasteners between the front panel and the one side. A secondary adjustment may also be made between the opposite side and the front panel to fine-tune the adjustment.

In a preferred embodiment according to the present invention, there is provided an orthotic device comprising an orthotic body having back and front panels and sides interconnecting the front and back panels for encompassing an individual's torso, the back panel having upper and lower regions angularly related to one another to simulate a posterior lumbar lordosis of the individual and an adjustment mechanism mounted on the back panel for adjusting the angular relation of the upper and lower regions of the device to enable the shape of the back panel to closely follow the shape of the individual's back.

In a further preferred embodiment according to the present invention, there is provided an orthotic device comprising an orthotic body having back and front panels and sides interconnecting the front and back panels for encompassing an individuals torso, the back panel having upper and lower regions angularly related to one another to generally correspond to the posterior lumbar lordosis of the individual and one of the sides being attached to the front panel by a pair of generally vertically spaced fasteners cooperable between the one side and the front panel to adjust the girth of the body about the individual's torso.

DETAILED DESCRIPTION OF THE INVENTION

Figure 1:
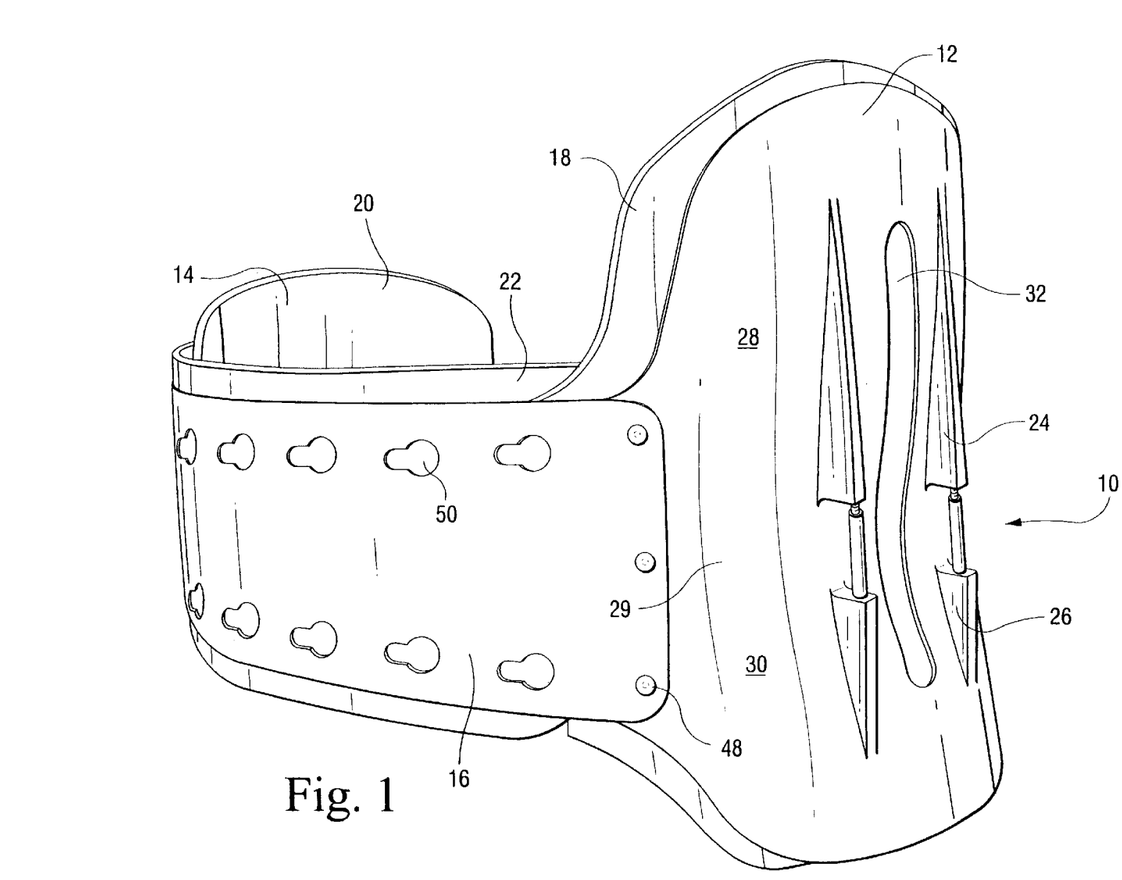
FIG. 1 is a perspective view of a posterior lumbar lordosis orthotic device constructed in accordance with a preferred embodiment of the present invention.

Referring now to the drawings, particularly to FIG. 1, there is illustrated a posterior lumbar lordosis orthotic device, generally designated 10, including a back panel 12, a front panel 14 and sides 16. The front and back panels 12 and 14, respectively, and sides 16 are preferably formed of a semi-rigid or semi-flexible plastic material such as molded polyethylene. Each of the front and back panels and sides have an interior resilient and flexible liner 18, 20 and 22, respectively, such as a foam material formed of expanded open-cell polyethylene, rendering the orthotic device comfortable when donned by the individual.

Figure 2:
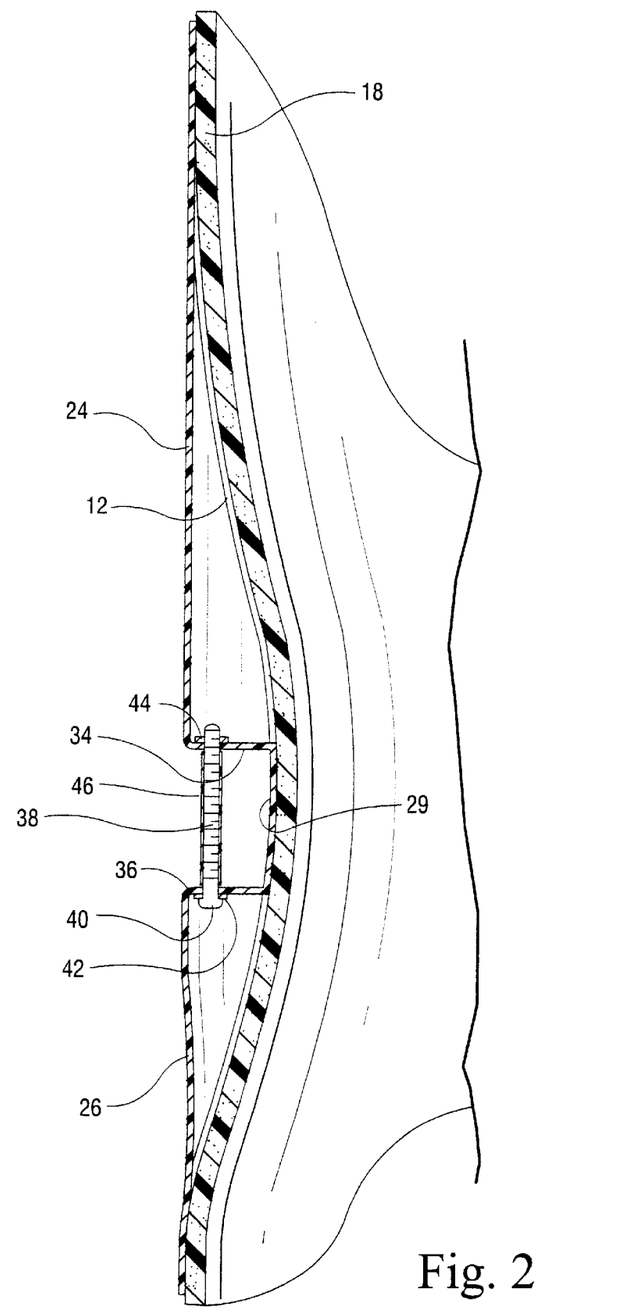
FIG. 2 is an enlarged fragmentary cross-sectional view through the back panel illustrating a mechanism for adjusting the angle of the back panel to adjust the device to an individual's lordosis.
Figure 3:
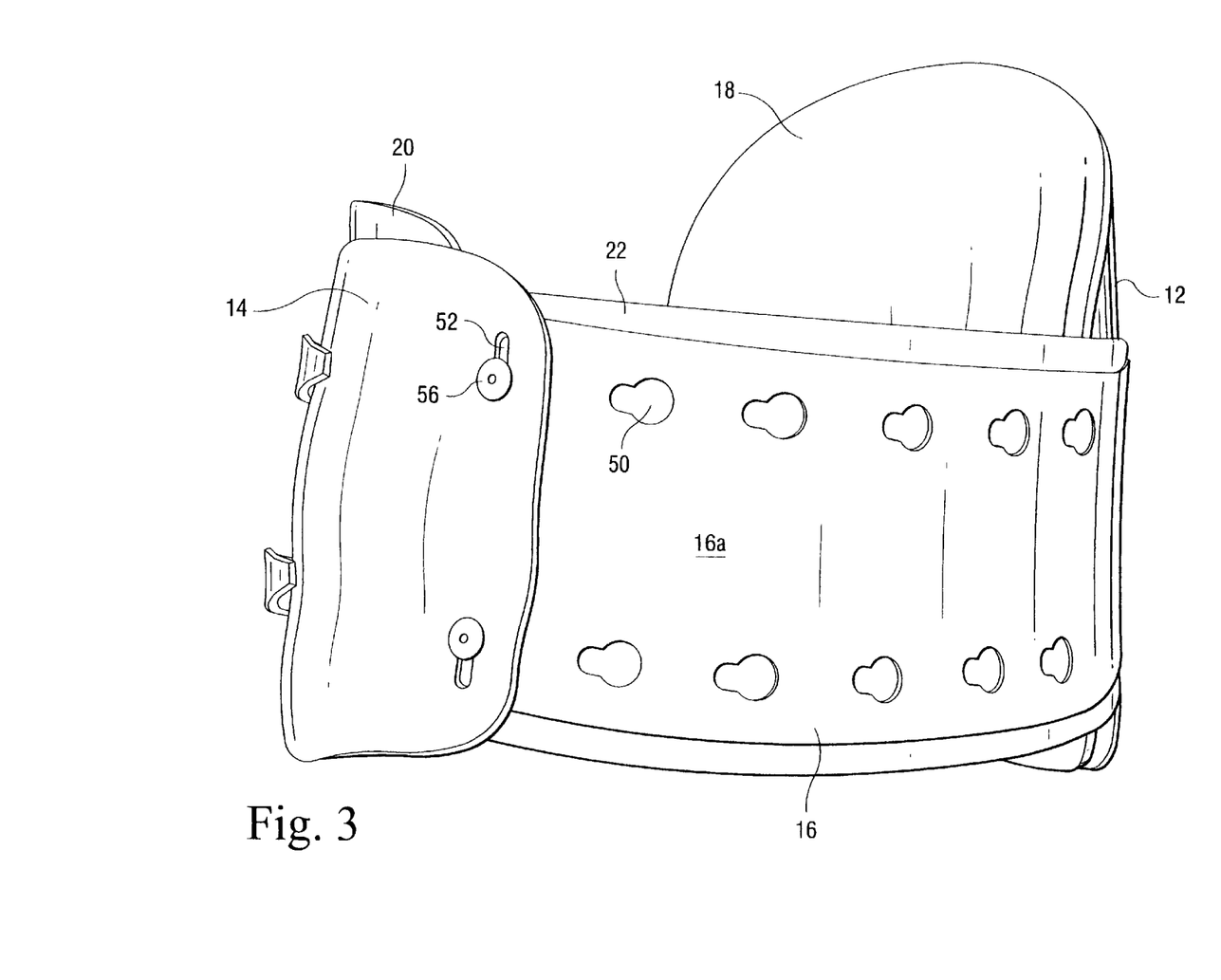
FIG. 3 is a perspective view of the orthotic device illustrating portions of the front panel and a side.

As illustrated in FIGS. 1 and 2, the back panel 12 includes pairs of outwardly extending, laterally spaced reinforcements 24 and 26 carried by upper and lower regions 28 and 30, respectively, of the back panel 12. The reinforcements are molded into the back panel 12 and essentially comprise tapered channel sections projecting rearwardly from the back panel along its outside surface. The pairs of reinforcements 24 and 26 also straddle a central opening 32 through the back panel exposing a portion of the open-cell liner 18 and affording a flexibility to the back panel. The generally channel-shaped reinforcements 24 and 26 terminate in enlarged ends having end faces 34 and 36, respectively (FIG. 2), in spaced opposition to one another. The upper and lower regions 28 and 30 straddle or lie on opposite sides of a waist region 29.

Spanning between each exposed pair of end faces 34 and 36 is an elongated rod 38, preferably a threaded bolt as illustrated (FIG. 2), having a head 40 at one end including a washer 42. At the opposite end of the rod 38 is a nut 34 fixed against rotation in a slot for threadedly receiving the threaded end of the rod 38. It will be appreciated that by rotating rod 38 in a direction tending to tighten the screw relative to the nut 44, the upper and lower regions 28 and 30 will tend to increase the angle between one another, as measured along the inside face of the back panel 12, i.e., increase the lordotic angle. By rotating the rod 38 in the opposite direction, unthreading the mating screw threads of the rod and nut relative to one another, the angle between the upper and lower regions 28 and 30, respectively, of the back panel 12 may be decreased. It will be appreciated that the upper and lower regions 28 and 30 are shaped to generally correspond to the average posterior lumbar lordosis of an individual, i.e., about 10–20°. That is to say, the back panel 12 is molded to simulate the shape of the average lumbar region of an individual. However, the angular relationship between the upper and lower regions 28 and 30 can be adjusted to increase or decrease the lordotic angle by tightening and loosening, respectively, the mating threads of the rods 38 and nuts 44. Access to the head 40 of rod 38 is provided from the interior side of the back panel. The liner 18 of the back panel, as well as the liners for the sides and front panel, are preferably releasably secured along the interior face of each panel and side, for example, by Velcro®, whereby the liners can be removed. By removing the liner 18 or opening a space between the liner and the back panel 12, access may be obtained to the head 40 of the rod 38 whereby a screwdriver can be inserted to rotate the rod 38 to increase or decrease the angle between the upper and lower regions 28 and 30, respectively, as desired. As illustrated in FIGS. 1 and 2, a sleeve 46 is disposed about the rod 38 between the end faces 34 and 36 of the reinforcements 24 and 26. By rotating the rods, the angle between the upper and lower regions 28 and 30 of the back panel 12 can be adjusted such that the back panel 12 is adjustable to complement the lordosis of the individual wearing the device thereby to support the individuals back.

Figure 4:
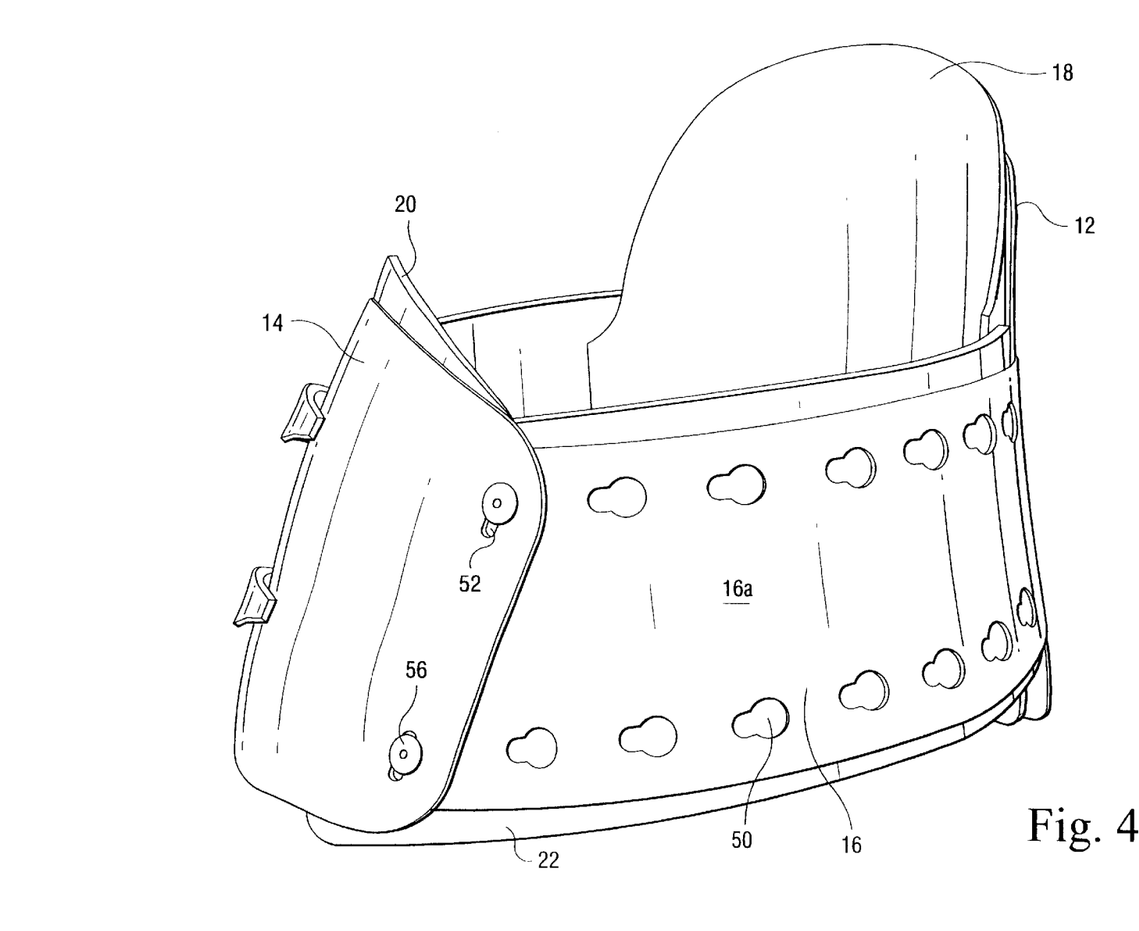
FIG. 4 is a view similar to FIG. 3 illustrating a differential girth adjustment.

Referring now to FIG. 4, there is illustrated an adjustable connection between the front panel and one of the sides 16*a*. It will be appreciated that the sides 16 are fixed, for example, by rivets 48 (FIG. 1), to the opposite side margins of the back panel 12. Along each of the sides 16 are provided a plurality of laterally spaced, horizontally extending key slots 50 aligned in a circumferential or girth direction along and adjacent upper and lower margins of the sides. That is, the key slots 50 are spaced vertically one from the other, forming vertically aligned pairs thereof at horizontally spaced locations along the upper and lower margins of sides 16. Key slots 52 are also provided along the margin on one side of the front panel 14. Key slots 52, however, extend away from one another in opposite vertical directions. Fasteners 56 are provided to join the front panel 14 and side 16*a* to one another. Particularly, the fasteners include a pop rivet having an added dual disk as described below, for securing the front panel 14 and side 16*a* to one another in adjustable positions.

A feature of the present invention resides in the capacity of the fasteners to not only adjust the gross girth of the device about the torso of the individual but to differentially adjust the gross girth of the device at vertically spaced locations about the torso. For example, where an individual may have a thin waist and a large hip development, the upper fastener can be shifted horizontally the distance between horizontally adjacent keyhole slots such that the upper fastener defines a girth about an upper portion of the orthotic device less than the girth the lower fastener 56 affords along a lower portion of the device. In this manner, differential girths in the waist and hip regions of different individuals may be accommodated by a single orthotic device shaped to accommodate an average-sized individual.

Figure 5:
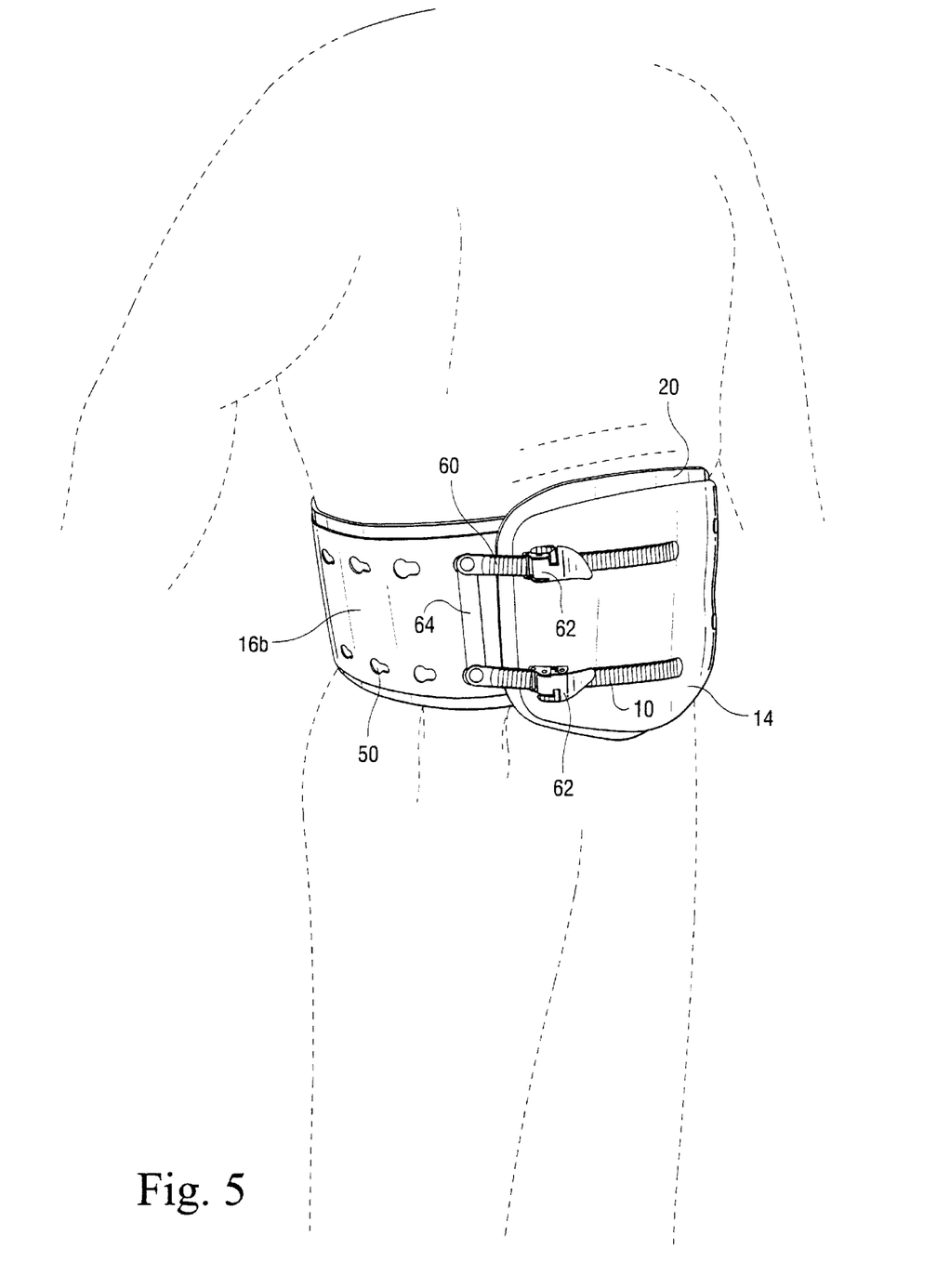
FIG. 5 is a perspective view of the orthotic device illustrating the front panel and another side of the device.
Figure 6:
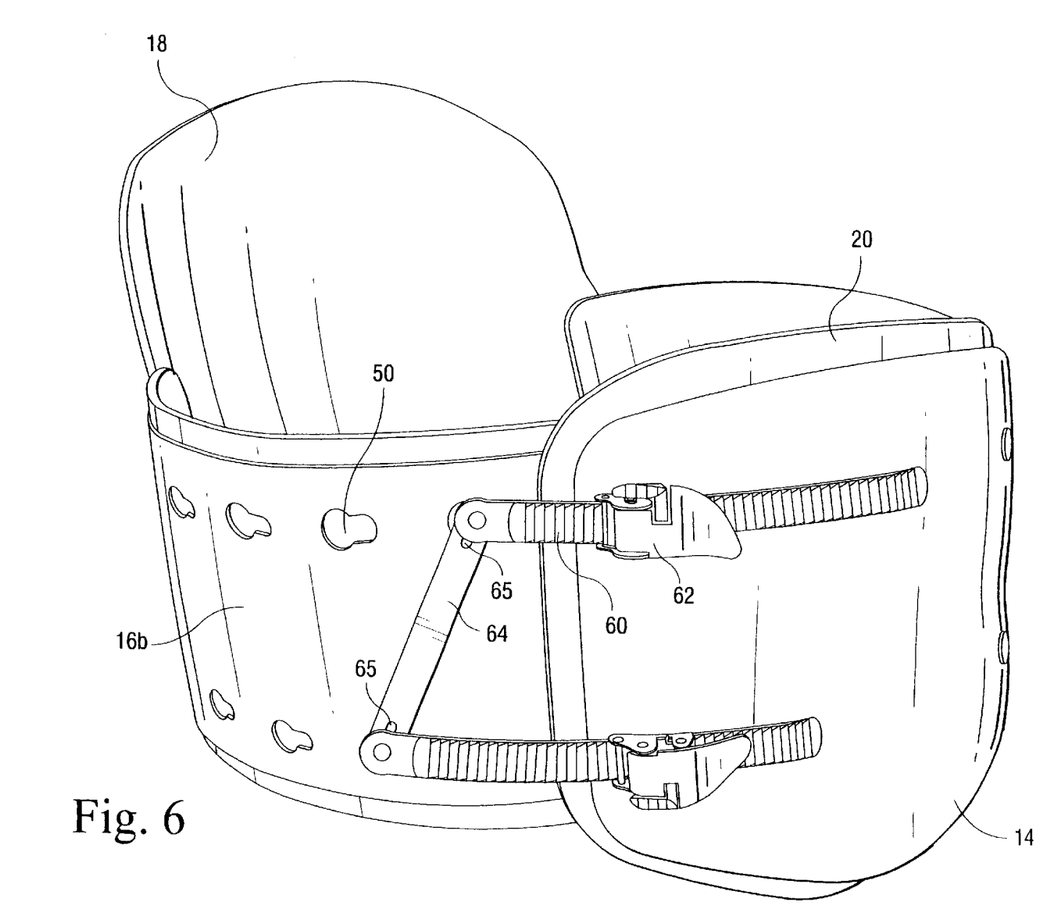
FIG. 6 is a fragmentary enlarged perspective view of straps for connecting the another side of the device to the front panel for fine adjustment.
Figures 7, 8, 9:
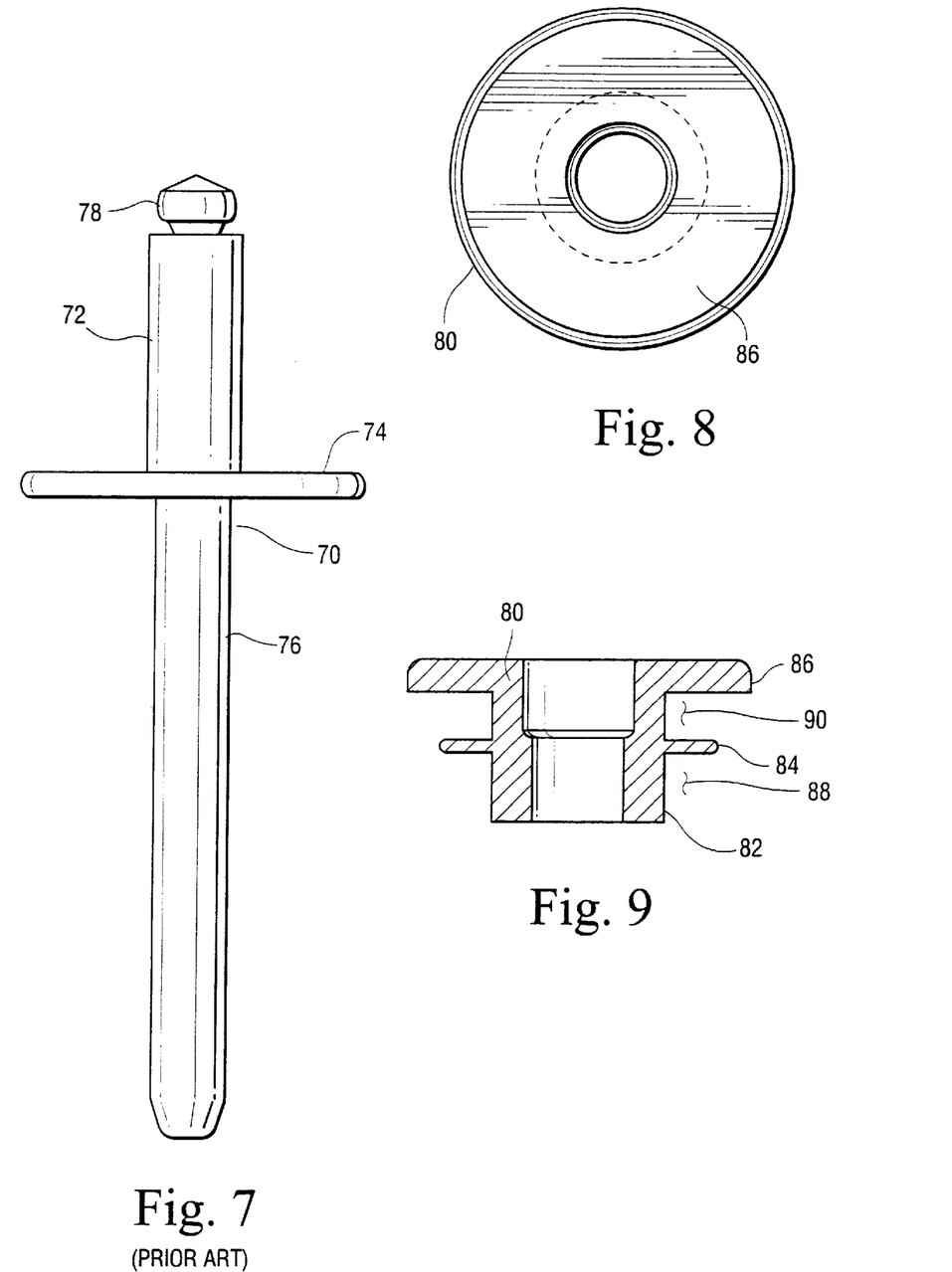
FIG. 7 is an enlarged elevational view of a prior art pop rivet.
FIG. 8 is a plan view of a disk for use with the pop rivet of FIG. 7 to form a unique feature.
FIG. 9 is a cross-sectional view of the disk of FIG. 8.
Figure 10:
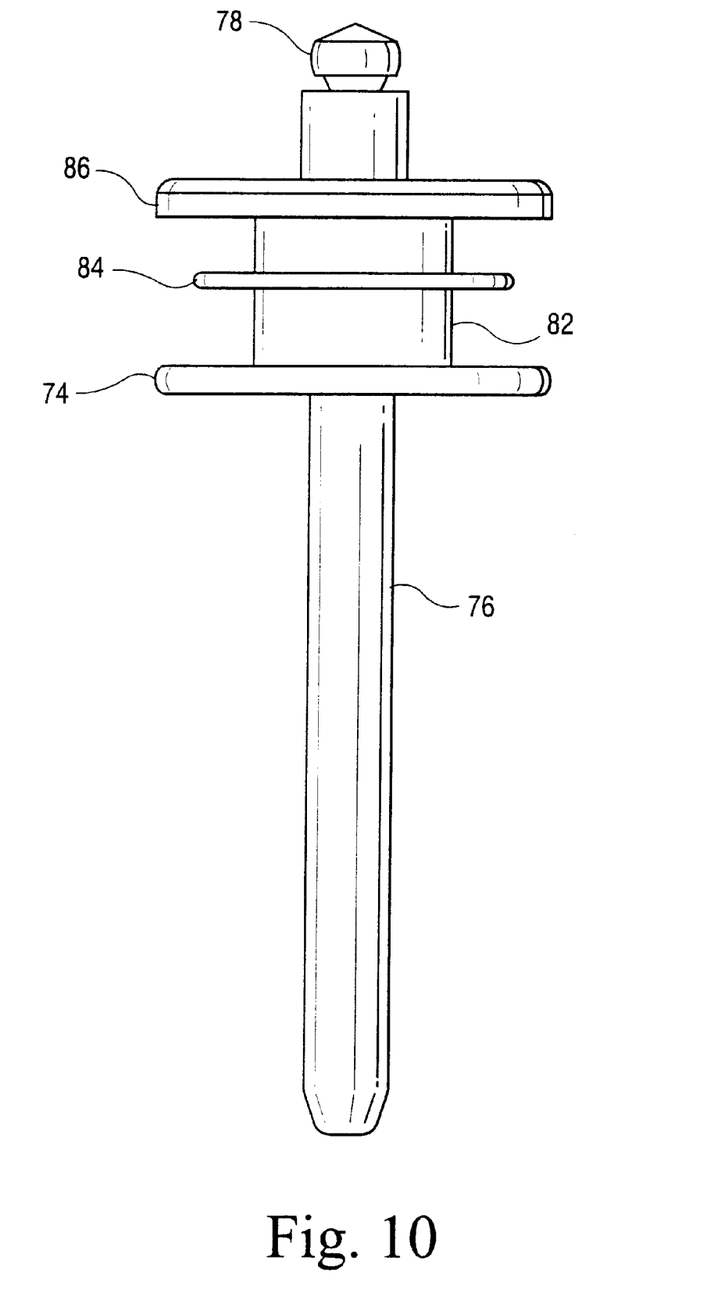
FIG. 10 is a side elevational view of the fastener prior to application.

The opposite side 16*b* and the edge of the front panel 14 are secured by adjustable straps 60 (FIGS. 5 and 6). A pair of buckles 62 are secured along the front side of the front panel at vertically spaced positions relative to one another. Straps 60 have ratchet teeth along their outer faces which cooperate with straps within the buckles 62. The straps terminate at distal ends 63 in a connecting link which joins the distal ends to one another. It will be appreciated that the straps and buckles cooperate to permit the straps to be extended from the buckles or retracted relative to the buckles, with the buckles locking the straps 60 in selected lengths between the buckles 62 and the link 64. Similarly as with the opposite side 16*a* of the front panel 14, the straps 60 are provided with modified pop rivets such that the distal ends of straps 60 can be releasably secured in the key slots 50 along the side 16*b* whereby the overall girth of the device can be adjusted. Additionally, the modified pop rivets of the upper and lower straps 60 may be shifted laterally relative to one another for securement to a key slot 50 offset in the lateral direction. To accommodate such differential adjustment, key slots 65 are provided in the link 64 so that link 64 can span between laterally offset key slots 50 along upper and lower margins of the side 16*b*. Thus, different girths between upper and lower portions of the orthotic device may be fine-tuned and accommodated by the straps 60 and link 64 arrangement.

Referring now to FIGS. 7–10, the modified rivet includes a conventional pop rivet 70 having a sleeve 72, a disk 74 and a pin 76 having an enlarged bulbous head 78. As conventional, two parts to be joined to one another are disposed over the sleeve 72 and the pin 76 is pulled to force the head 78 to enlarge the sleeve 72 on the opposite side of the parts from the disk 74. Using that pop rivet as a basis, the present invention also includes an annulus 80 comprised of an outer sleeve 82 and a pair of disks 84 and 86 spaced one from the other. By locating the outer sleeve 82 over the sleeve 72 of the prior art pop rivet 70, three disks 74, 84 and 86 are provided, with two annular spaces 88 and 90 between the three disks. By locating the margins of the key slots 50 and openings through the front panel within the respective annuli 88 and 90 and pulling the pin 76 to cause the sleeve 72 to enlarge over the disk 86, the modified pop rivet enables releasable securement of the front panel 14 to the side 16.

It will also be appreciated that the orthotic device is preferably molded into male and female shapes, i.e., the device is gender-specific. The differences reside primarily in the configuration of the back panel. For the female orthotic device, the lower region of the back panel has a broader curvature at its bottom and a smaller waist curvature. The male back panel is the reverse, as compared with the female back panel, i.e., a lesser curvature at the bottom of the back panel and a larger waist curvature. The gender-specific devices are also differentiated by color, e.g., gray for male and blue for female.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An orthotic device comprising:
   an orthotic body having back and front panels and sides interconnecting the front and back panels for encompassing an individual's torso;
   said back panel having upper and lower regions angularly related to one another to simulate a posterior lumbar lordosis of the individual; and
   an adjustment mechanism mounted on the back panel for adjusting the angular relation of the upper and lower regions of the device to enable the shape of the back panel to closely follow the shape of the individual's back.

2. A device according to claim 1 wherein said adjustment mechanism includes along an outside of the back panel an adjustable coupling between said angularly related upper and lower regions for altering the angle between said upper and lower regions.

3. A device according to claim 1 wherein said adjustment mechanism includes at least one elongated rod having opposite ends engaged with respective upper and lower regions of the back panel and a screw thread on said rod cooperable with a mating screw thread on the back panel to adjust the angle between said upper and lower regions upon relative rotation of the screw threads.

4. A device according to claim 3 wherein said rod has a portion accessible from an inside of said back panel for rotating said rod.

5. A device according to claim 3 including a second elongated rod having opposite ends engaged with the respective upper and lower regions of the back panel and a screw thread on said second rod cooperable with a second mating screw thread on the back panel to adjust the angle between said upper and lower regions upon relative rotation of the second screw threads, said rods being laterally spaced from one another.

6. A device according to claim 5 wherein said upper and lower regions have outwardly projecting reinforcements, respectively, for receiving opposite ends of the rods.

7. A device according to claim 1 wherein said adjustment mechanism includes a pair of laterally spaced elongated rods having opposite ends engaged with the respective upper and lower regions of the back panel, each of said rods having a screw thread cooperable with a mating screw thread on the back panel to adjust the angle between said upper and lower regions upon relative rotation of the respective mating screw threads, said upper and lower regions having outwardly projecting reinforcements, respectively, for receiving opposite ends of said rods.

8. A device according to claim 7 wherein each of said rods has a portion accessible from an inside of said back panel for rotating said rod.

9. A device according to claim 1 wherein one of said sides is attached to said front panel by a pair of generally vertically spaced fasteners cooperable between said one side and said front panel at laterally spaced positions to adjust the girth of the body about the individual's torso.

10. A device according to claim 9 wherein said pair of fasteners are cooperable to independently adjust the girth of the body at vertically spaced locations thereabout.

11. A device according to claim 9 wherein said pair of fasteners are cooperable to enlarge the girth of the body about a first location thereof without adjusting the girth of the body about a second location spaced vertically from said first location.

12. A device according to claim 9 wherein each of said fasteners includes a key-shaped slot in one of said sides and said front panel and a hook cooperable with said slot in another of said sides and said front panel.

13. A device according to claim 12 wherein said hook includes first, second and third axially spaced disks defining first and second annular spaces therebetween and connected to one another by an axially extending central sleeve, said first and second disks clamping about margins of said one side and said front panel and said second and third disks clamping about margins of said another of said sides and said front panel.

14. A device according to claim 13 wherein said first disk and said central sleeve comprise a pop rivet, said second and third disks being disposed on said central shaft and a portion of said central shaft overlying said third disk on a side thereof remote from said first and second disks to retain said second and third disks on said central shaft.

15. A device according to claim 1 wherein one of said sides is attached to said front panel by a pair of generally vertically spaced fasteners cooperable between said one side and said front panel to independently adjust the girth of the body at vertically spaced regions thereof, each said fastener including a slot in one of said sides and said front panel extending in a generally vertical direction and a pin in another of said sides and said front panel enabling an enlargement of the girth of the body about a first region thereof without adjusting the girth of the body about a second region spaced vertically from said first region.

16. An orthotic device comprising:
   an orthotic body having back and front panels and sides interconnecting the front and back panels for encompassing an individual's torso;
   said back panel having upper and lower regions angularly related to one another to generally correspond to the posterior lumbar lordosis of the individual;
   one of said sides being attached to said front panel by a pair of generally vertically spaced fasteners cooperable between said one side and said front panel to adjust the girth of the body about the individual's torso; and
   an adjustment mechanism including along an outside of the back panel an adjustable coupling between said angularly related upper and lower regions for altering the angle between said upper and lower regions.

17. A device according to claim 16 wherein said pair of fasteners are cooperable to enlarge the girth of the body about a first region thereof without adjusting the girth of the body about a second region spaced vertically from said first region.

18. A device according to claim 16 wherein said pair of fasteners are cooperable to independently adjust the girth of the body at vertically spaced regions thereof.

19. An orthotic device comprising:

an orthotic body having back and front panels and sides interconnecting the front and back panels for encompassing an individual's torso;

said back panel having upper and lower regions angularly related to one another to generally correspond to the posterior lumbar lordosis of the individual;

one of said sides being attached to said front panel by a pair of generally vertically spaced fasteners cooperable between said one side and said front panel to adjust the girth of the body about the individual's torso; and an adjustment mechanism including at least one elongated rod having opposite ends engaged with respective upper and lower regions of the back panel and a screw thread on said rod cooperable with a mating screw thread on the back panel to adjust the angle between said upper and lower regions upon relative rotation of the screw threads.

20. A device according to claim 19 wherein said pair of fasteners are cooperable to independently adjust the girth of the body at vertically spaced regions thereof.

21. A device according to claim 19 wherein said pair of fasteners are cooperable to enlarge the girth of the body about a first region thereof without adjusting the girth of the body about a second region spaced vertically from said first region.

22. An orthotic device comprising:

an orthotic body having back and front panels interconnected with one another for encompassing an individual's torso;

said back panel having upper and lower regions angularly related to one another to generally correspond to the posterior lumbar lordosis of the individual; and an adjustment mechanism mounted on the back panel for adjusting the angular relation of the upper and lower regions of the back panel to enable the shape of the back panel to closely follow the shape of the individual's back, said adjustment mechanism including an adjustable coupling between said angularly related upper and lower regions for altering the angle between the upper and lower regions.

\* \* \* \* \*